(12) United States Patent  (10) Patent No.: US 9,771,518 B2
Lin et al.  (45) Date of Patent: Sep. 26, 2017

(54) PHOTO RESPONSIVE MATERIAL AND OPTICAL DEVICE

(71) Applicant: INDUSTRIAL TECHNOLOGY RESEARCH INSTITUTE, Hsinchu (TW)

(72) Inventors: Chien-Wen Lin, Luzhu Township (TW); Yi-Lang Tsai, Taichung (TW); Jong-Lieh Yang, Hsinchu (TW); Shih-Hsien Liu, Jhubei (TW); Chao-Wu Liaw, New Taipei (TW); Kung-Lung Cheng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 57 days.

(21) Appl. No.: 14/983,840

(22) Filed: Dec. 30, 2015

(65) Prior Publication Data

US 2017/0166814 A1 Jun. 15, 2017

(30) Foreign Application Priority Data

Dec. 9, 2015 (TW) .............................. 104141253 A

(51) Int. Cl.
C09K 19/00 (2006.01)
C09K 19/34 (2006.01)
(Continued)

(52) U.S. Cl.
CPC ........ C09K 19/3483 (2013.01); C07D 405/10 (2013.01); C07D 311/92 (2013.01); Y10T 428/10 (2015.01); Y10T 428/1036 (2015.01)

(58) Field of Classification Search
CPC .. C09K 19/3483; C09K 19/60; C07D 405/10; C07D 311/92; C09B 57/00; G02B 1/041;
(Continued)

(56) References Cited

U.S. PATENT DOCUMENTS 8,436,184 B2 5/2013 Aiken et al.
8,697,890 B2 4/2014 Sukhomlinova et al.
(Continued)

FOREIGN PATENT DOCUMENTS

TW 200833672 A 8/2008

OTHER PUBLICATIONS

Taiwanese Notice of Allowance, dated Jul. 6, 2016, for Taiwanese Application No. 104141253.
(Continued)

Primary Examiner — Ruiyun Zhang
(74) Attorney, Agent, or Firm — Birch, Stewart, Kolasch & Birch, LLP

(57) ABSTRACT

An optical device is provided, which includes a first transparent substrate, a second transparent substrate, and a liquid-crystal material disposed between the first transparent substrate and the second transparent substrate. The liquid-crystal material includes a photo responsive material with a chemical structure of:

wherein $A^1$ is (Continued)

-continued

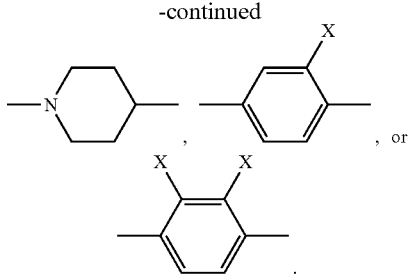

$A^2$ and $A^3$ are independently

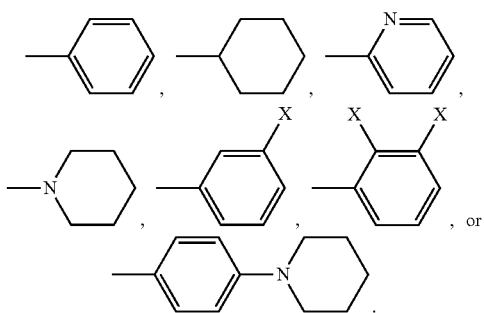

X is halogen. R is H, $C_{1-12}$ alkyl group, or $C_{1-12}$ alkoxy group. R' is $C_{1-12}$ alkyl group.

6 Claims, 1 Drawing Sheet

(51) Int. Cl.
*C07D 405/10* (2006.01)
*C07D 311/92* (2006.01)

(58) Field of Classification Search
CPC ... G02B 5/23; Y10T 428/10; Y10T 428/1036; Y10T 428/1041
USPC ............ 428/1.1, 1.3, 1.31; 349/13, 16, 165; 252/299.1, 586; 546/196; 548/525; 549/389
See application file for complete search history.

(56) References Cited

U.S. PATENT DOCUMENTS

| | | |
|---|---|---|
| 8,703,978 B2 | 4/2014 | Aiken et al. |
| 9,028,728 B2 | 5/2015 | Bancroft et al. |
| 2014/0197361 A1* | 7/2014 | Sukhomlinova ..... C07D 311/92 252/299.1 |

OTHER PUBLICATIONS

Delbaere et al., "Unexpected Halogen Substituent Effects on the Complex Thermal Relaxation of Naphthopyrans after UV Irradiation", J. Org. Chem. 70, pp. 5302-5304, 2005.
Kosa et al., "Light-induced liquid crystallinity", Nature, vol. 485, pp. 347-349, May 17, 2012.
Malic et al., "Controlling Molecular Mobility in Polymer Matrices: Synchronizing Switching Speeds of Multiple Photochromic Dyes", Macromolecules, 43, pp. 8488-8501, 2010.
Sousa et al., "Photochromic Fused-Naphthopyrans without Residual Color", The Journal of Organic Chemistry, 77, pp. 3959-3968, 2012.
White et al., "Dynamic color in stimuli-responsive cholestric liquid crystals", Journal of Materials Chemistry, 20, pp. 9832-9847, 2010.

* cited by examiner

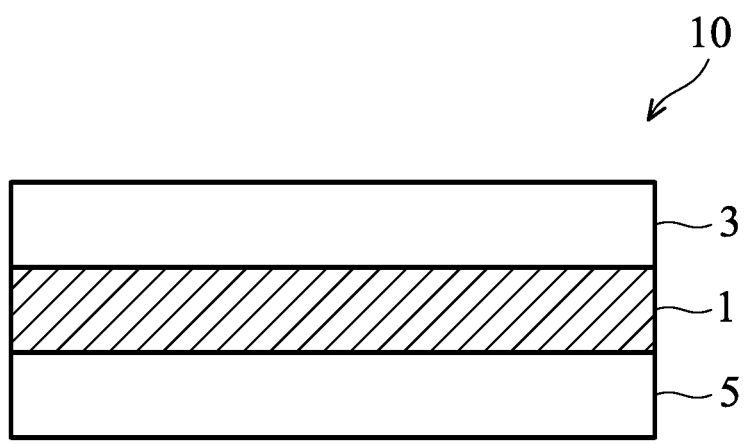

PHOTO RESPONSIVE MATERIAL AND OPTICAL DEVICE

CROSS REFERENCE TO RELATED APPLICATIONS

The present application is based on, and claims priority from, Taiwan Application Serial Number 104141253, filed on Dec. 9, 2015, the disclosure of which is hereby incorporated by reference herein in its entirety.

TECHNICAL FIELD

The technical field relates to a photo responsive material and an optical device utilizing the photo responsive material.

BACKGROUND

Photochromism is a known physical phenomenon that occurs in some compounds, and detailed discussion of how it works can be found in Photochromism Molecules and Systems (Studies in Organic Chemistry, Vol. 40., Edited by H. Durr and H. Bouas-Laurent, Elsevier, 1990). Pyran derivatives are conventional photochromic compounds, which have adsorption wavelength at their excitation state.

A photochromic material can be applied as a color transition lens, smart window, window film, or other photochromic applications, which need a fast and reversible photochromic characteristic. However, conventional photochromic materials have a relatively low UV adsorption coefficient (low UV sensitivity). Conventional photochromic materials also need a long time to reinstate to a transparent state. In other words, even if the conventional photochromic materials are not irradiated by UV anymore, they still cannot quickly reinstate back to transparency. In addition, conventional photochromic materials have a high melting point and poor solubility, making them difficult to process and requiring the addition of other materials (e.g. liquid-crystal, solvent, or polymer) for improving their processability. Accordingly, a novel photochromic material for overcoming the above shortcomings is called for.

SUMMARY

One embodiment of the disclosure provides a photo responsive material, having a chemical structure of:

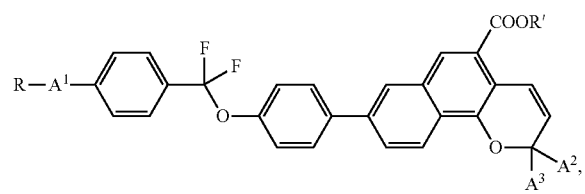

wherein $A^1$ is

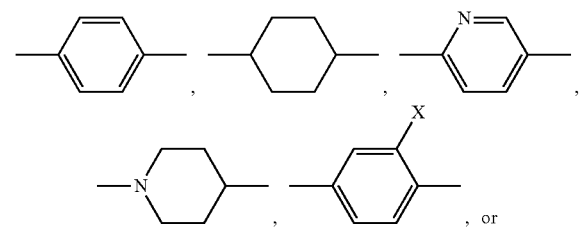

, or

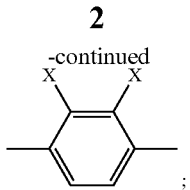

;

$A^2$ and $A^3$ are independently

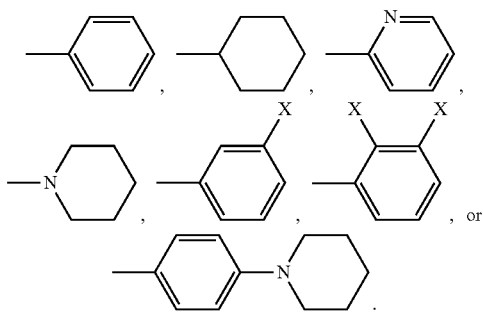

wherein X is halogen; R is H, $C_{1-12}$ alkyl group, or $C_{1-12}$ alkoxy group; and R' is $C_{1-12}$ alkyl group.

One embodiment of the disclosure provides an optical device, comprising: a first transparent substrate; a second transparent substrate; and a liquid-crystal material disposed between the first transparent substrate and the second transparent substrate, wherein the liquid-crystal material includes a photo responsive material with a chemical structure of:

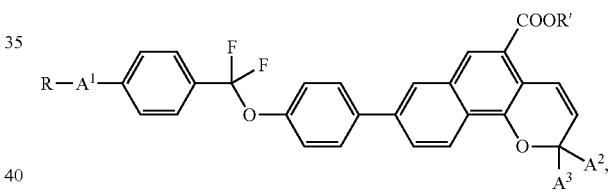

wherein $A^1$ is

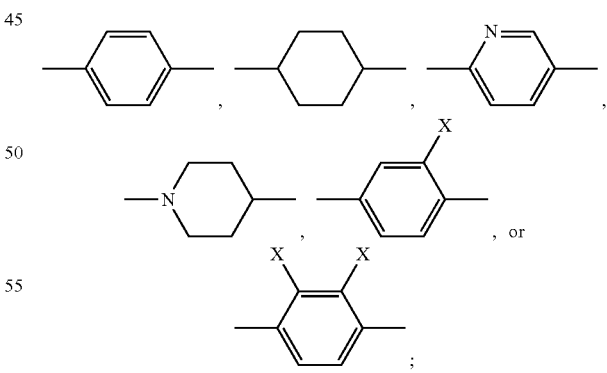

;

$A^2$ and $A^3$ are independently

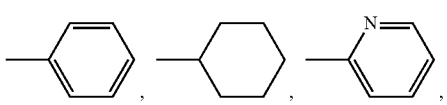

-continued

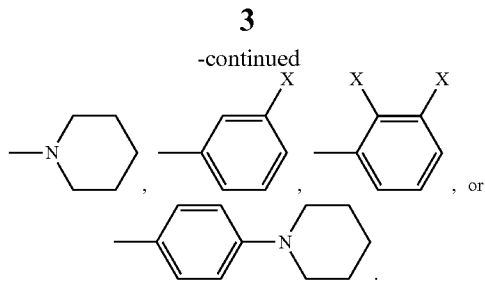

X is halogen, R is H, $C_{1-12}$ alkyl group, or $C_{1-12}$ alkoxy group, and R' is $C_{1-12}$ alkyl group.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 shows an optical device in one embodiment of the disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment provides a photo responsive material with a chemical structure as shown in Formula 1.

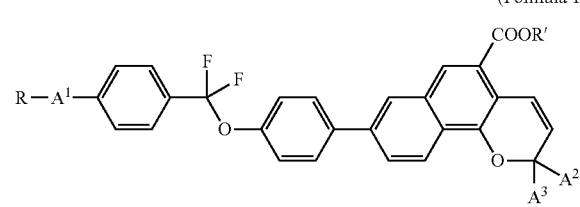
(Formula 1)

In Formula 1, $A^1$ is

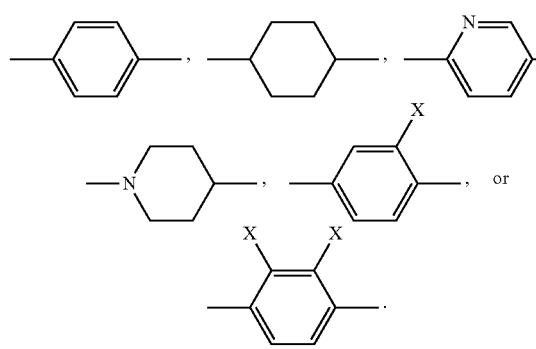

$A^2$ and $A^3$ are independently

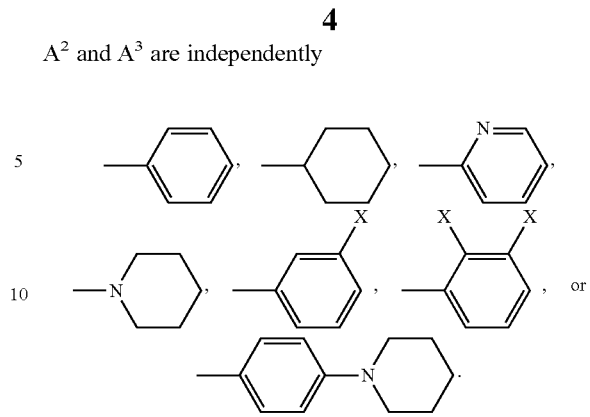

X is halogen. R is H, $C_{1-12}$ alkyl group, or $C_{1-12}$ alkoxy group. R' is $C_{1-12}$ alkyl group.

In one embodiment, the photo responsive material is synthesized as indicated below. Note that the following synthesis strategy is only for illustration, and one skilled in the art may choose other synthesis methods to form the photo responsive material on the basis of his/her own equipment and raw materials.

First, halogenated aldehyde, dialkyl ester, and a base are heated to react, as shown in Formula 2. In Formula 2, X is halogen, and R' is $C_{1-12}$ alkyl group.

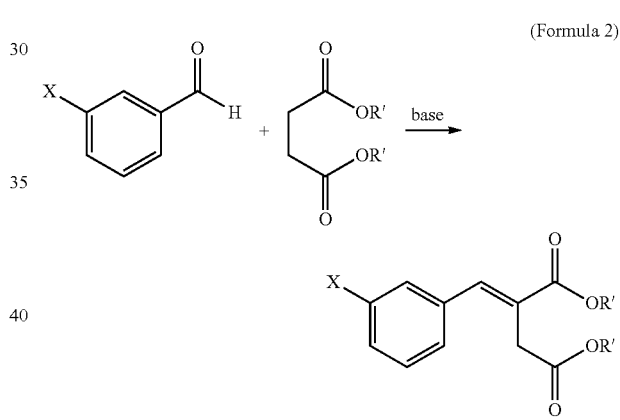
(Formula 2)

Subsequently, the product in Formula 2, sodium acetate, and acetic anhydride are refluxed to react, as shown in Formula 3.

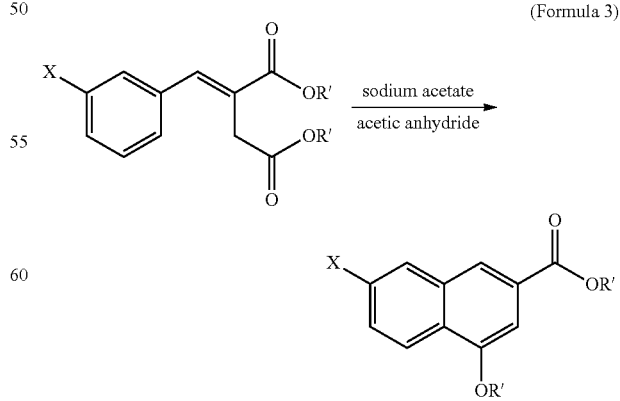
(Formula 3)

Subsequently, the product in Formula 3 and the potassium carbonate are refluxed to react, as shown in Formula 4.

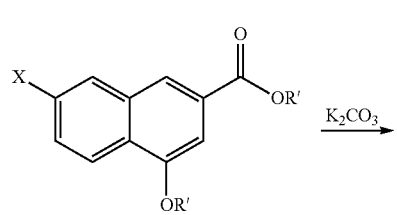

(Formula 4)

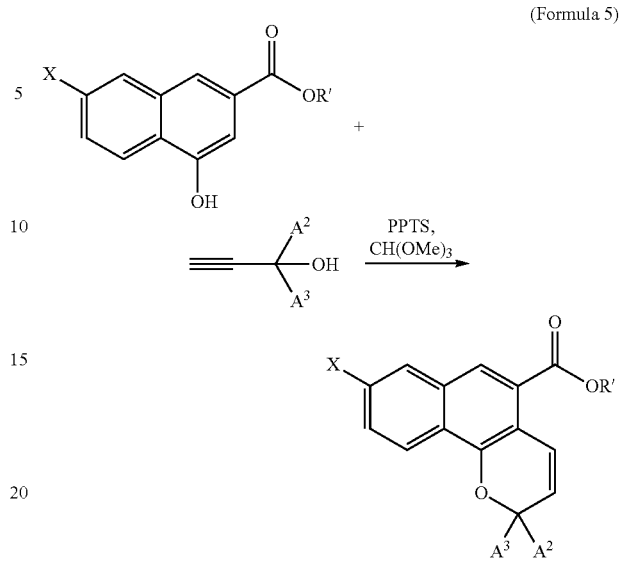

(Formula 5)

Subsequently, the product in Formula 4, an alkyne compound, trimethyl orthoformate, and pyridinium p-toluenesulfonate (PPTS) are reacted, as shown in Formula 5. In Formula 5, definitions of $A^2$ and $A^3$ are similar to those described above.

Subsequently, the product in Formula 5, 1,3,2-dioxaborolane, sodium carbonate, and tetrakis(triphenylphosphine) palladium(0) are reacted as a Suzuki coupling to obtain a photo responsive material, as shown in Formula 6. In Formula 6, definitions of $A^1$ and R are similar to those described above.

(Formula 6)

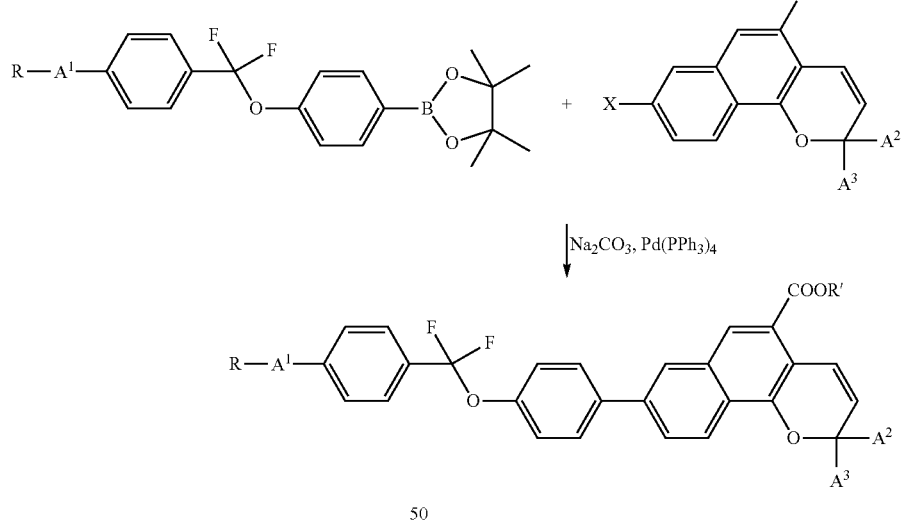

In one embodiment, the photo responsive material has a chemical structure of Formula 7 or Formula 7. In Formulae 7 and 8, a definition of R is similar to that described above.

(Formula 7)

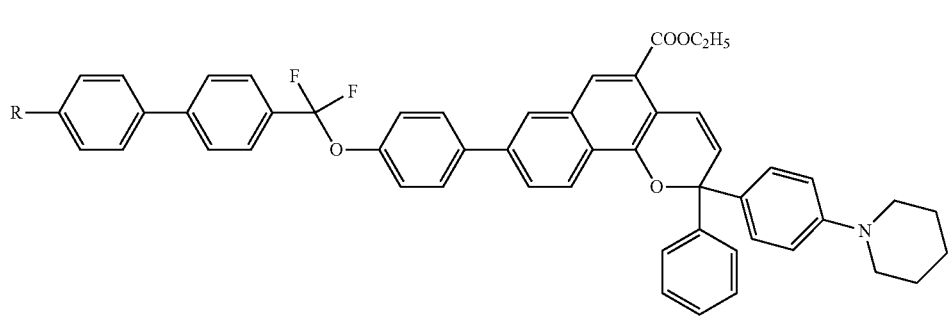

-continued (Formula 8)

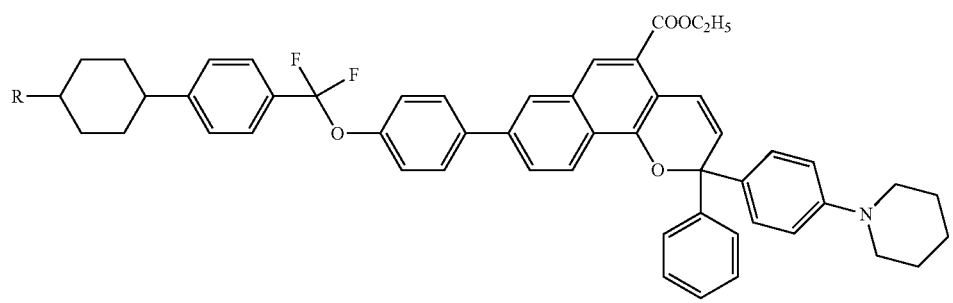

In one embodiment, several liquid-crystal materials can be pre-mixed to form a liquid-crystal host material, and the photo responsive material is then added into the liquid-crystal host material to form a liquid-crystal material 1. The liquid-crystal material 1 can be disposed between transparent substrates 3 and 5 to complete an optical device 10, as shown in FIG. 1. In one embodiment, the transparent substrates 3 and 5 are composed of same or different materials, such as a rigid substrate (e.g. glass or quartz) or a flexible substrate (e.g. plastic). An optical device 10 is colorless when it is not irradiated by UV, but rapidly turns to be opaque of a dark color when it is irradiated by UV. The optical device 10 of the dark color will reinstate to be colorless after removing the UV irradiation for a while. The color transition progress is a reversible phenomenon, so that the optical device 10 can be utilized as a color transition lens, a smart window, a window film, or in other photochromic applications.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

0.33 moles of potassium t-butoxide and 500 mL of t-butanol were added into a two-neck bottle (1 L) to be stirred until completely dissolved. 0.3 moles of tribromo aldehyde, 0.3 moles of diethyl succinate, and 100 mL of t-butanol were mixed and then slowly and dropwise added into the two-neck bottle. The mixture was heated to 100° C. and reacted at 100° C. for 4 hours. The reaction result was then cooled to room temperature, and extracted by ethyl acetate and water several times. The ethyl acetate layer was collected, dried by anhydrous MgSO$_4$, and filtered. The filtrate was concentrated to obtain a pale yellow liquid product (106 g, yield=96%). The reaction is shown in Formula 9.

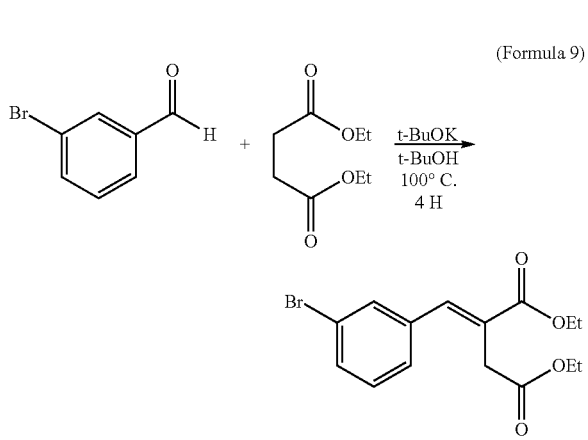

(Formula 9)

Subsequently, 0.288 moles of the product in Formula 9, 0.316 moles of sodium acetate, and 0.5 moles of acetic anhydride were added into a two-neck bottle (500 mL) to be stirred until completely dissolved, and then heated to 140° C. and refluxed and reacted at 140° C. for 6 hours. The reaction result was then cooled to room temperature, and the acetic anhydride was vacuumed out. The concentrated reaction result was then extracted by ethyl acetate and water several times. The ethyl acetate layer was collected, dried by anhydrous MgSO$_4$, and filtered. The filtrate was concentrated to obtain a brown liquid product (77 g, yield=75%). The reaction is shown in Formula 10.

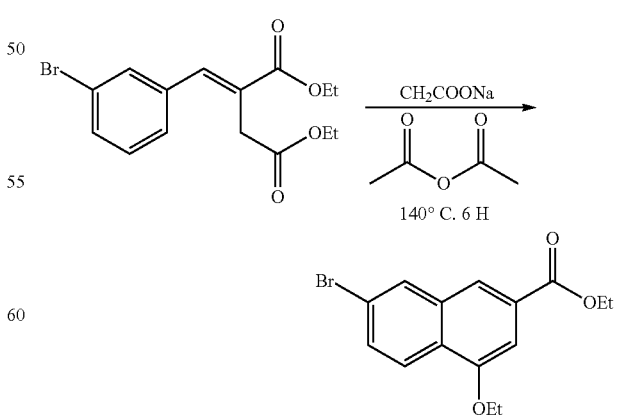

(Formula 10)

0.216 moles of the product in Formula 10, 0.324 moles of potassium carbonate, and 150 mL of ethanol were added into a two-neck bottle (250 mL) to be stirred until completely dissolved, and then heated to 80° C. and refluxed and reacted at 80° C. for 4 hours. The reaction result was then cooled to room temperature, and the ethanol was vacuumed out. The concentrated reaction result was then extracted by ethyl acetate and water several times. The ethyl acetate layer was collected, dried by anhydrous MgSO$_4$, and filtered. The filtrate was concentrated to obtain a pale yellow liquid product (106 g, yield=95%). The reaction is shown in Formula 11.

(Formula 11)

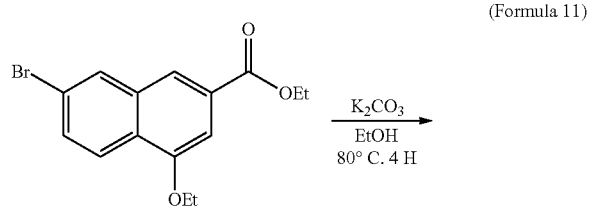

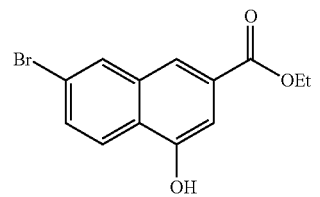

0.194 moles of the product in Formula 11, 0.194 moles of 1-phenyl-1-[4-(1-piperidinyl)phenyl]-2-propyn-1-ol, 0.388 moles of and 150 mL of trimethyl orthoformate, and 150 mL of dichloromethane were added into a two-neck bottle (250 mL) to be stirred until completely dissolved. 0.097 moles of pyridinium p-toluenesulfonate (PPTS) was then added into the two-neck bottle, and the mixture was then heated to reflux overnight. The reaction result was then cooled to room temperature, and then extracted by dichloromethane and water several times. The dichloromethane layer was collected, dried by anhydrous MgSO$_4$, and filtered. The filtrate was concentrated to obtain a brown liquid product (5.76 g, yield=52.5%). The reaction is shown in Formula 12.

(Formula 12)

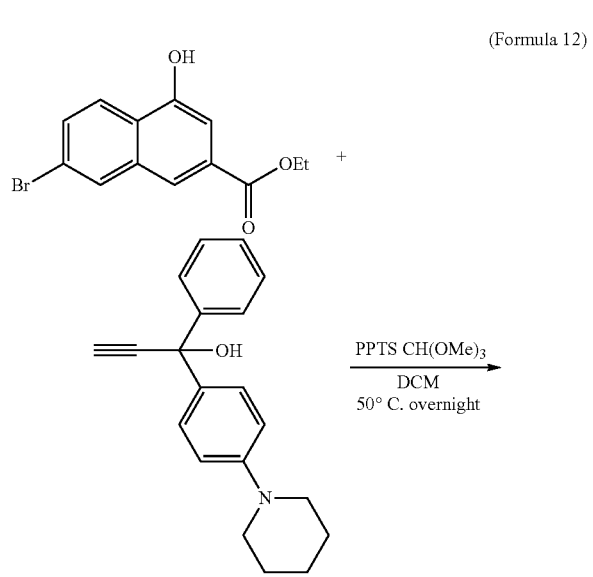

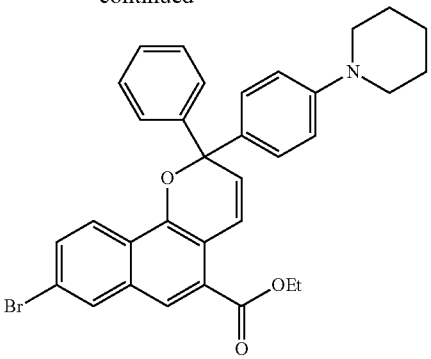

1 mole of 4-(4-hexylphenyl)benzoic acid was dissolved in 100 mL of toluene and 100 mL of isooctane. 1.5 moles of 1,3-propanedithiol was dropwise added into the above solution, and the solution was heated to 50° C. 1.5 moles of trifluoromethanesulfonate was then dropwise added into the above solution, and the solution was heated to 110° C. and reacted at 110° C. for about 4 to 6 hours. The reaction result was then cooled to room temperature, and then stood to precipitate yellow solid product (9.7 g, yield was about 86%). The reaction is shown in Formula 13.

(Formula 13)

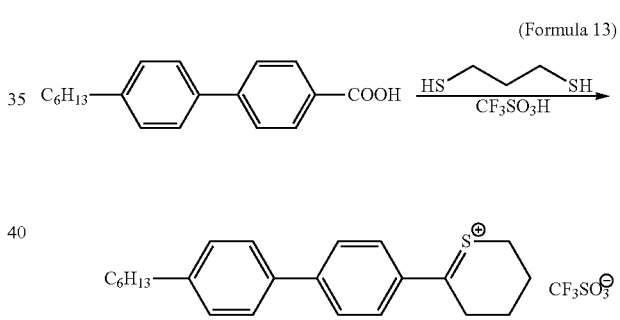

1 mole of the product in Formula 13 was dissolved in 150 mL of dichloromethane, and then cooled to −68° C. 1.2 moles of 4-bromophenol and 1.2 moles of triethylamine were dissolved in dichloromethane, and then dropwise added to the solution of the product in Formula 13 to react at −68° C. for 1 hour, wherein the solution color was changed from yellow to colorless. The reaction was continued at −68° C. for another 1 hour, thereby precipitating yellow solid from a white suspension during the reaction. The pH value of the reaction result liquid is tuned to 5 to 8 by a NaOH solution (1M). Thereafter, the alkalized liquid was extracted by dichloromethane (300 mL) and saline (300 mL). The dichloromethane layer was collected, dried by anhydrous MgSO$_4$, and filtered. The filtrate was concentrated and re-crystallized by dichloromethane/hexane (1/20), and then vacuumed at room temperature for 3 hours to obtain a white solid product (6.8 g, yield=78%). The reaction is shown in Formula 14.

(Formula 14)

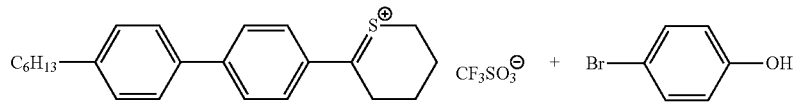

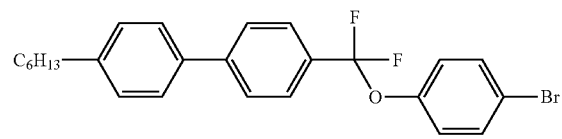

1 mole of the product in Formula 14, 2 moles of bis(pinacolato)diboron, and 3.4 moles of potassium acetate were dissolved in toluene, and stirred to react for 30 minutes. 0.02 moles of tetrakis(triphenylphosphine)palladium(0) was then added into the above solution and then stirred for further 30 minutes, and the mixture was then heated to 120° C. to react overnight. The reaction result was cooled to room temperature, and then extracted by ethyl acetate (300 mL) and saline (300 mL). The ethyl acetate layer was collected, dried by anhydrous $MgSO_4$, and filtered. The filtrate was concentrated and re-crystallized by dichloromethane/methanol (1/20), and then vacuumed at room temperature for 3 hours to obtain a white solid product (6.8 g, yield=90.6%). The reaction is shown in Formula 15.

(Formula 15)

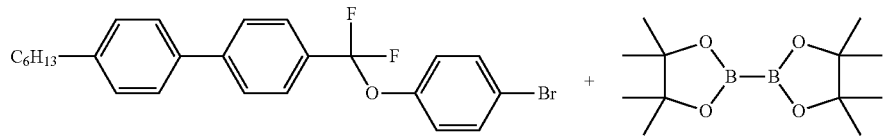

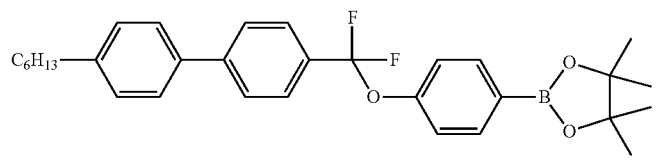

0.102 moles of the product in Formula 12, 0.102 moles of the product in Formula 15, 0.4 moles of sodium carbonate, and 300 mL of toluene were added into a two-neck bottle (500 mL) to be stirred until completely dissolved. 0.01 moles of tetrakis(triphenylphosphine)palladium(0) was then added into the above solution, and the mixture was heated to 100° C. and reacted at 100° C. for 6 hours. The reaction result was cooled to room temperature, and then extracted by ethyl acetate and water several times. The ethyl acetate layer was collected, dried by anhydrous $MgSO_4$, and filtered. The filtrate was concentrated to obtain a brown crude. The crude was re-crystallized by dichloromethane/methanol (1/2) to obtain a pale purple solid, which was then vacuumed at room temperature for 8 hours to remove solvent thereof for obtaining a pale purple solid product (6.75 g, yield=85.8%). The reaction is shown in Formula 16.

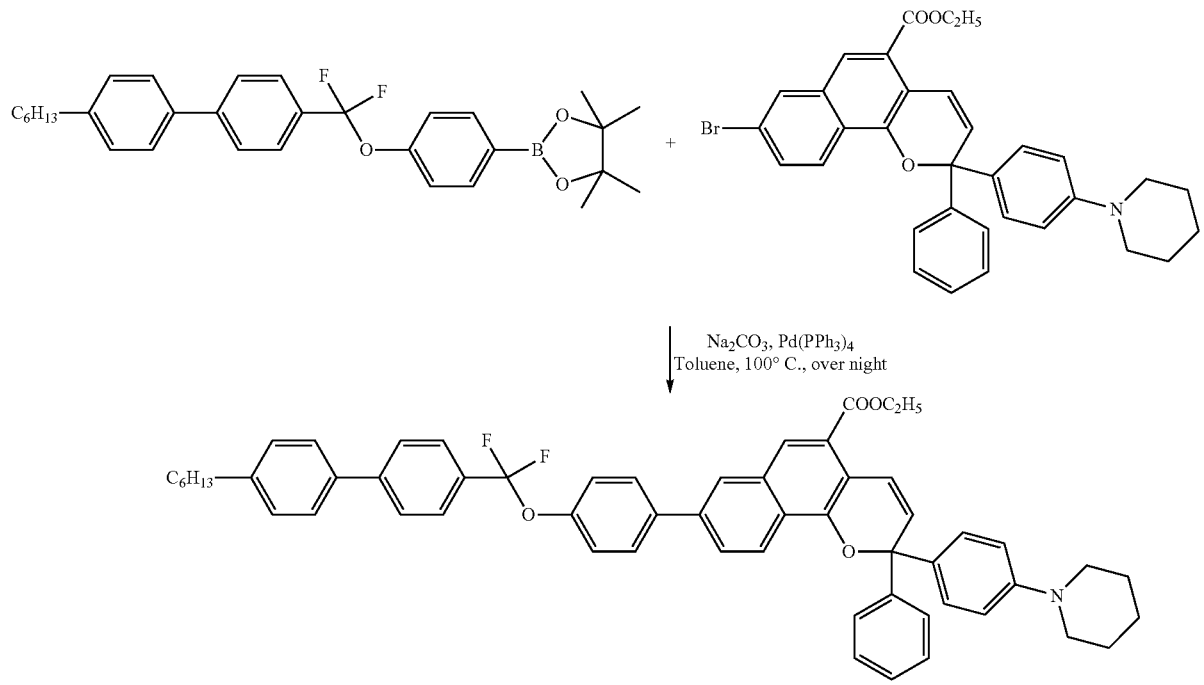

(Formula 16)

The product in Formula 16 had spectra as below: $^1$H NMR (400 MHz, Acetone-$d_6$) δ 8.50 (d, 1H), 8.23 (d, 1H), 8.19 (s, 1H), 8.00 (t, 1H), 7.89(t, 4H), 7.83 (d, 2H), 7.67 (s, 1H), 7.64 (d, 2H), 7.59 (d, 2H), 7.57 (s, 2H), 7.48 (d, 2H), 7.40 (s, 2H), 7.37 (d, 2H), 7.33 (t, 1H), 6.86 (d, 2H), 6.43 (d, 1H), 6.39 (d, 2H), 3.10 (t, 4H), 2.67 (t, 2H), 1.63 (d, 3H), 1.63 (d, 3H), 1.59 (s, 2H), 1.58 (s, 2H), 1.40(t, 2H), 1.33 (m, 4H), 1.28 (m, 4H), 0.87 (t, 3H). ESI-Mass: calcd for $C_{58}H_{55}F_2N_1O_4$: 868.06, found: 868.4715.

0.00868 g of the product in Formula 16 was dissolved in dichloromethane to form a transparent solution (10 mL). 1 mL of the dichloromethane solution was diluted by dichloromethane to 10 mL, and the dilution process was repeated 3 times to form a test solution with a concentration of $1 \times 10^{-6}$M. The test solution was put into a transparent quartz cell with a width of 1cm, and then analyzed by UV/Vis spectrometer (SLM-468) to measure its UV-Vis adsorption spectrum. The maximum adsorption spectrum intensity of the test solution was then calculated by Beer's Law (A=ϵ b c), thereby obtaining an adsorption coefficient (ϵ) of the product in Formula 16 ($1.02 \times 10^6$).

A host material of a liquid-crystal material was formulated according to the composition and ratio in Table 1. The product in Formula 16 was then added into the host material and heated to 80° C. to be completely dissolved, and then cooled to room temperature to form the liquid-crystal material. The liquid-crystal material was then siphoned to inject into a liquid-crystal test cell (TN-mode 22 μm test cell), and sealed for further tests. The test sample was put on an instrument for measuring response time (DMS-803c). First, the light transmittance of the test sample not irradiated by UV was defined as a base line. The liquid-crystal material in the test cell was then irradiated by a handheld UV lamp with a wavelength of 365 nm for 2 minutes, and the appearance of which was changed from colorless to deep purple. The UV lamp was then quickly moved away, and the light transmittance change of the test sample was evaluated by DMS-803c, thereby calculating the period for the light transmittance of the test sample reinstating back to 100% (photo response time of the liquid-crystal material). The additive amount, the reinstating period, and the maximum addition amount (more addition would be precipitated and not dissolved) of the product in Formula 16 are tabulated in Table 2.

TABLE 1

(Composition of the host material)

| Parts by weight | Chemical structures of monomers |
|---|---|
| 15 | $C_5H_{11}$—⟨cyclohexyl⟩—⟨phenyl⟩—⟨phenyl⟩—CN |
| 14 | $C_2H_5$—⟨phenyl⟩—⟨phenyl⟩—CN |
| 34 | $C_5H_{11}$—⟨phenyl⟩—⟨phenyl⟩—CN |
| 13 | $C_2H_5$—⟨phenyl⟩—COO—⟨phenyl⟩—CN |
| 15 | $C_3H_7$—⟨phenyl⟩—⟨phenyl⟩—CN |

TABLE 1-continued (Composition of the host material)

| Parts by weight | Chemical structures of monomers |
|---|---|
| 10 | 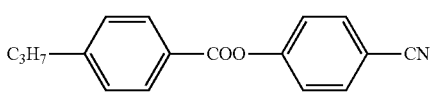 |

Example 2

1 mole of 4-(4-pentylcyclohexyl)benzoic acid was dissolved in 100 mL of toluene and 100 mL of isooctane. 1.5 moles of 1,3-propanedithiol was dropwise added into the above solution, and the solution was heated to 50° C. 1.5 moles of trifluoromethanesulfonate was then dropwise added into the above solution, and the solution was heated to 110° C. and reacted at 110° C. for about 4 to 6 hours. The reaction result was then cooled to room temperature, and then stood to precipitate yellow solid product (9.7 g, yield was about 86%). The reaction is shown in Formula 17.

(Formula 17)

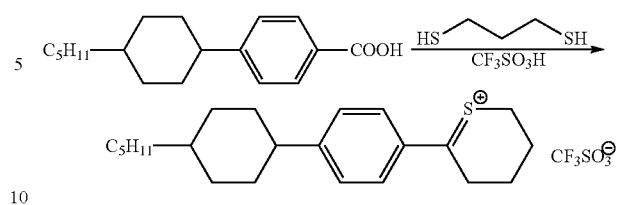

1 mole of the product in Formula 17 was dissolved in 150mL of dichloromethane, and then cooled to −68° C. 1.2 moles of 4-bromophenol and 1.2 moles of triethylamine were dissolved in dichloromethane, and then dropwise added to the solution of the product in Formula 17 to react at −68° C. for 1 hour, wherein the solution color was changed from yellow to colorless. The reaction was continued at −68° C. for another 1 hour, thereby precipitating yellow solid from a white suspension during the reaction. The pH value of the reaction result liquid is tuned to 5 to 8 by a NaOH solution (1M). Thereafter, the alkalized liquid was extracted by dichloromethane (300 mL) and saline (300 mL). The dichloromethane layer was collected, dried by anhydrous $MgSO_4$, and filtered. The filtrate was concentrated and re-crystallized by dichloromethane/hexane (1/20), and then vacuumed at room temperature for 3 hours to obtain a white solid product (6.8 g, yield=78%). The reaction is shown in Formula 18.

(Formula 18)

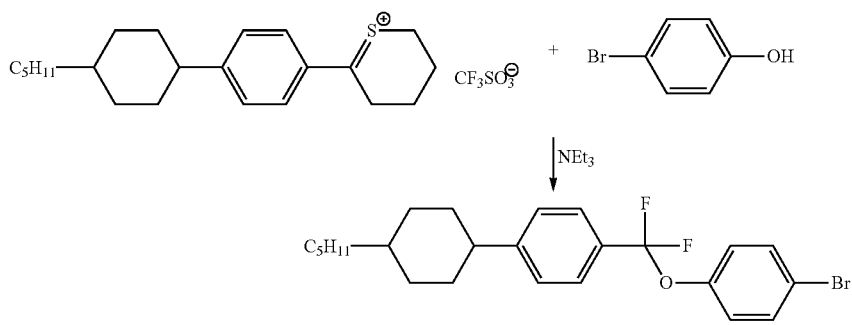

1 mole of the product in Formula 18, 2 moles of bis(pinacolato)diboron, and 3.4 moles of potassium acetate were dissolved in toluene, and stirred to react for 30 minutes. 0.02 moles of tetrakis(triphenylphosphine)palladium(0) was then added into the above solution and then stirred for further 30 minutes, and the mixture was then heated to 120° C. to react overnight. The reaction result was cooled to room temperature, and then extracted by ethyl acetate (300 mL) and saline (300 mL). The ethyl acetate layer was collected, dried by anhydrous $MgSO_4$, and filtered. The filtrate was concentrated and re-crystallized by dichloromethane/methanol (1/20), and then vacuumed at room temperature for 3 hours to obtain a white solid product (6.8 g, yield=90.6%). The reaction is shown in Formula 19.

(Formula 19)

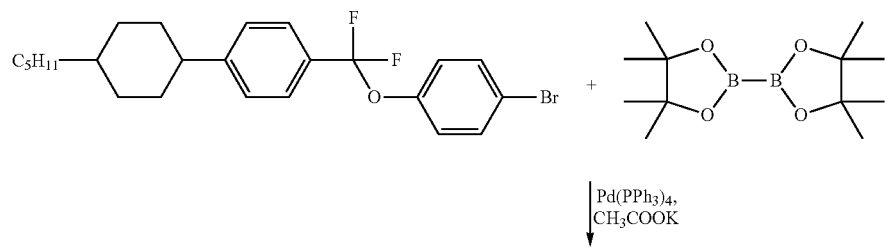

-continued

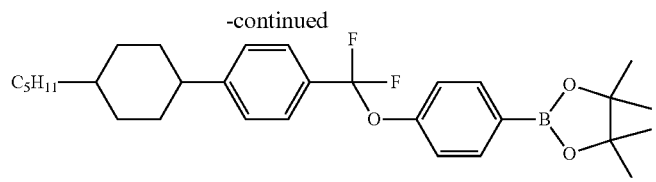

0.102 moles of the product in Formula 12, 0.102 moles of the product in Formula 19, 0.4 moles of sodium carbonate, and 300 mL of toluene were added into a two-neck bottle (500mL) to be stirred until completely dissolved. 0.01 moles of tetrakis(triphenylphosphine)palladium(0) was then added into the above solution, and the mixture was heated to 100° C. and reacted at 100° C. for 6 hours. The reaction result was cooled to room temperature, and then extracted by ethyl acetate and water several times. The ethyl acetate layer was collected, dried by anhydrous $MgSO_4$, and filtered. The filtrate was concentrated to obtain a brown crude. The reaction is shown in Formula 20. The crude was re-crystallized by dichloromethane/methanol (1/2) to obtain a pale purple solid, which was then vacuumed at room temperature for 8 hours to remove solvent thereof for obtaining a pale purple solid product (6.52 g, yield=84.5%).

The product in Formula 20 had spectra as below: $^1$H NMR (400 MHz, Acetone-$d_6$) δ 8.50 (d, 1H), 8.23 (d, 1H), 8.19 (s, 1H), 8.00 (t, 1H), 7.89(dd, 2H), 7.69(dd, 2H), 7.59 (d, 1H), 7.57 (d, 2H), 7.43 (dd, 4H), 7.35(q, 4H), 7.25 (t, 1H), 6.87 (d, 2H), 6.44 (d, 2H), 6.39 (dd, 2H), 3.11 (t, 4H), 2.78 (t, 1H), 1.88 (d, 4H), 1.59 (t, 4H), 1.53 (dd, 4H), 1.40(t, 3H), 1.31 (m, 9H), 1.28 (dd, 2H), 0.89 (t, 3H). ESI-Mass: calcd for $C_{57}H_{59}F_2N_1O_4$: 860.08, found: 860.4502.

The adsorption coefficient (ε) of the product in Formula 20 was $1.06 \times 10^6$, which was measured and calculated by the method described in Example 1.

In addition, the addition amount, the reinstating period, and the maximum addition amount of the product in Formula 20 was measured by the methods described in Example 1, as shown in Table 2.

Comparative Example 1

The compound in Formula 21 was synthesized by the method disclosed in U.S. Pat. No. 8,697,890.

(Formula 20)

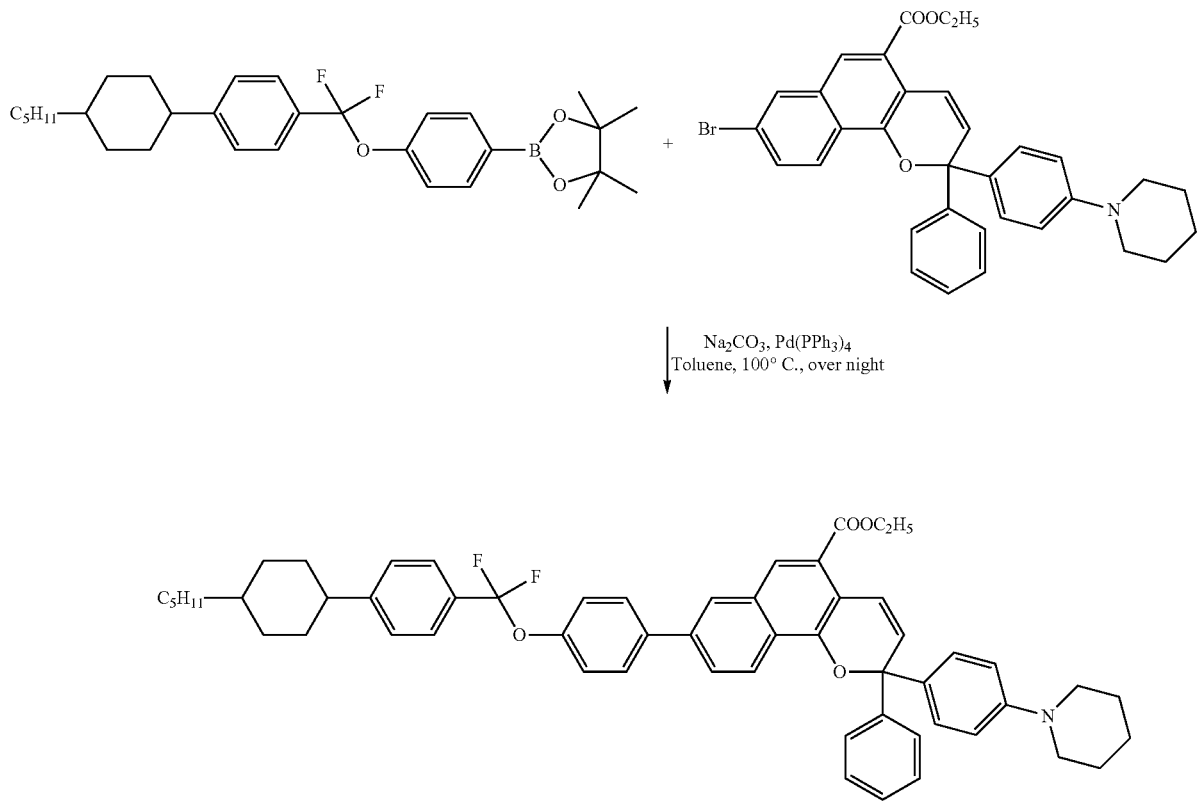

(Formula 21)

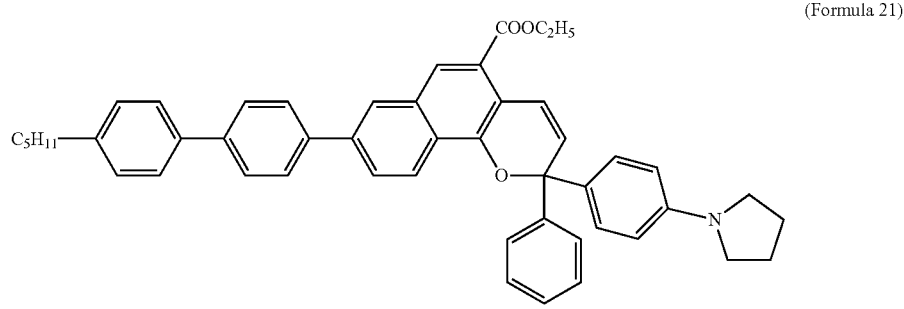

The adsorption coefficient (ε) of the compound in Formula 21 was 8.21×10⁵, which was measured and calculated by the method described in Example 1.

In addition, the addition amount, the reinstating period, and the maximum addition amount of the compound in Formula 21 was measured by the methods described in Example 1, as shown in Table 2.

Comparative Example 2

The compound in Formula 22 was synthesized by the method disclosed in U.S. Pat. No. 8,697,890.

(Formula 22)

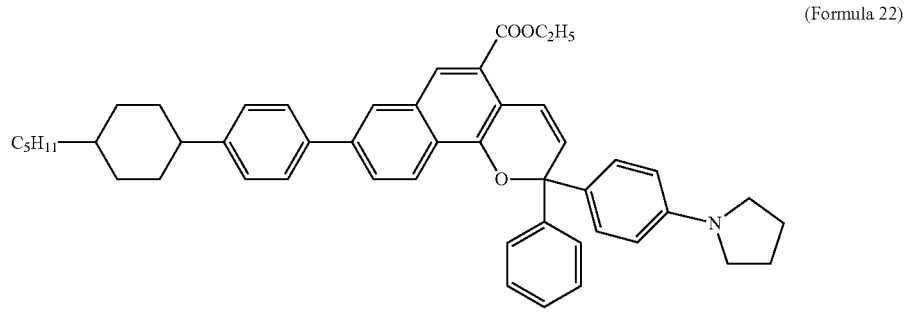

The adsorption coefficient (ε) of the compound in Formula 22 was 8.23×10⁵, which was measured and calculated by the method described in Example 1.

In addition, the addition amount, the reinstating period, and the maximum addition amount of the compound in Formula 22 was measured by the methods described in Example 1, as shown in Table 2.

TABLE 2

|  | Comparative Example 1 | Comparative Example 2 | Example 1 | | Example 2 | |
| --- | --- | --- | --- | --- | --- | --- |
| Adsorption coefficient(ε) | 8.21 × 10⁵ | 8.23 × 10⁵ | 1.02 × 10⁶ | | 1.06 × 10⁶ | |
| Addition amount (Parts by weight) | 6 | 6 | 6 | 8 | 6 | 8 |
| Reinstating time (Second) | 17.5 | 22.9 | 15.7 | 16.7 | 15.7 | 16.6 |
| Maximum addition amount (Parts by weight) | 8 | 8 | | 12 | | 12 |

As shown in comparison of Table 2, the photo responsive materials with a —CF₂O— group had a higher adsorption coefficient, a shorter reinstating period, and a higher addition amount (a higher solubility), thereby efficiently improving a performance of an optical device utilizing the same. For example, the photochromic device can be more sensitive due to the faster color change mechanism. In addition, the photo responsive materials are easier to be collocated with a host material of liquid-crystal in application.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A photo responsive material, having a chemical structure of:

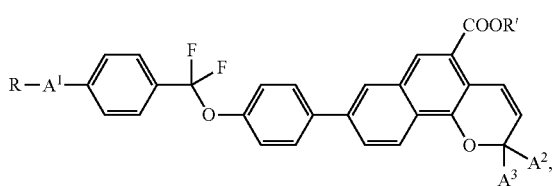

wherein A¹ is

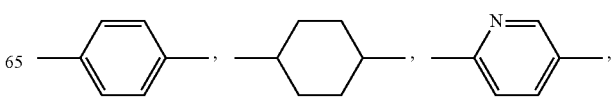

-continued

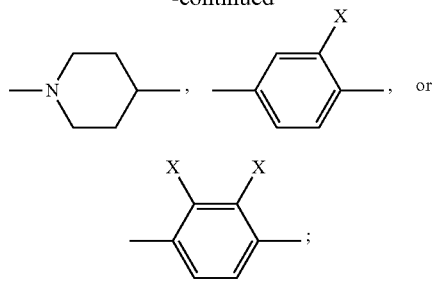

$A^2$ and $A^3$ are independently

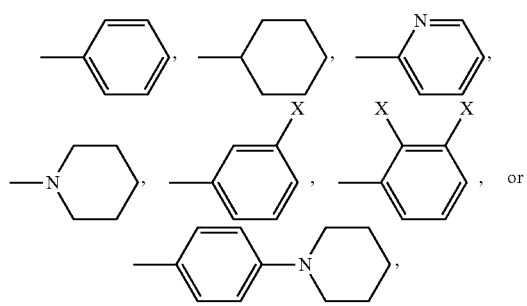

wherein X is halogen;
R is H, $C_{1-12}$ alkyl group, or $C_{1-12}$ alkoxy group; and
R' is $C_{1-12}$ alkyl group.

2. The photo responsive material as claimed in claim 1, having a chemical structure of:

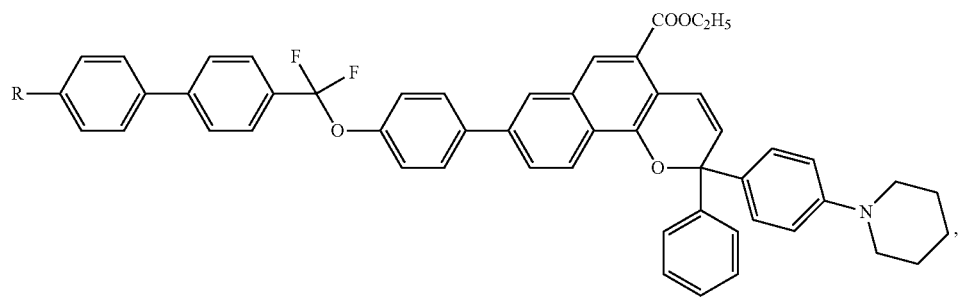

wherein R is $C_{1-12}$ alkyl group.

3. The photo responsive material as claimed in claim 1, having a chemical structure of:

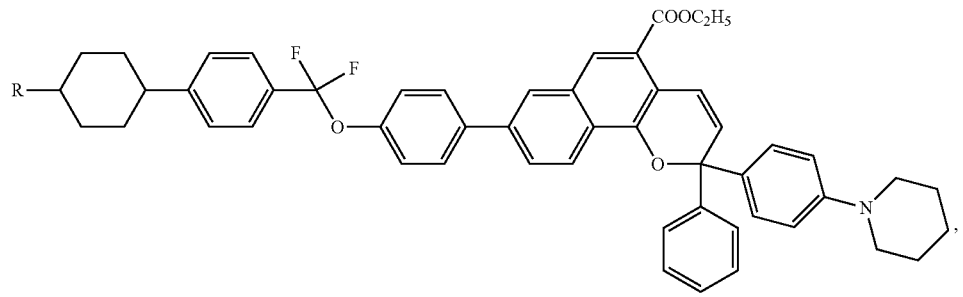

wherein R is $C_{1-12}$ alkyl group.

4. An optical device, comprising:
a first transparent substrate;
a second transparent substrate; and
a liquid-crystal material disposed between the first transparent substrate and the second transparent substrate,
wherein the liquid-crystal material includes a photo responsive material with a chemical structure of:

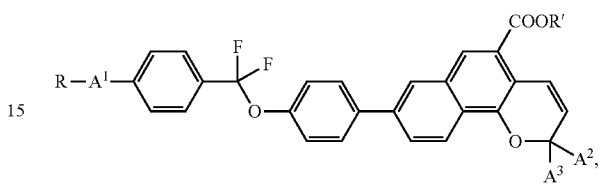

wherein $A^1$ is

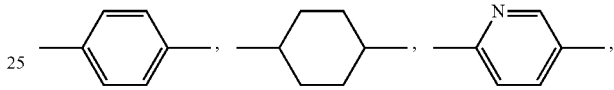

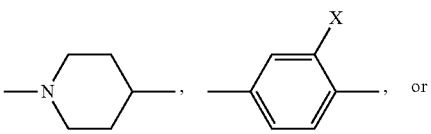

23

-continued

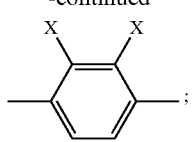

$A^2$ and $A^3$ are independently

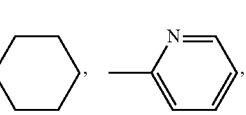

24

-continued

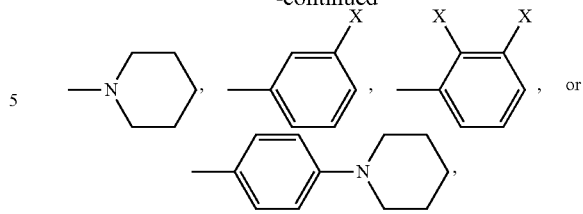

wherein X is halogen;
R is H, $C_{1-12}$ alkyl group, or $C_{1-12}$ alkoxy group; and
R' is $C_{1-12}$ alkyl group.

5. The optical device as claimed in claim 4, wherein the photo responsive material has a chemical structure of:

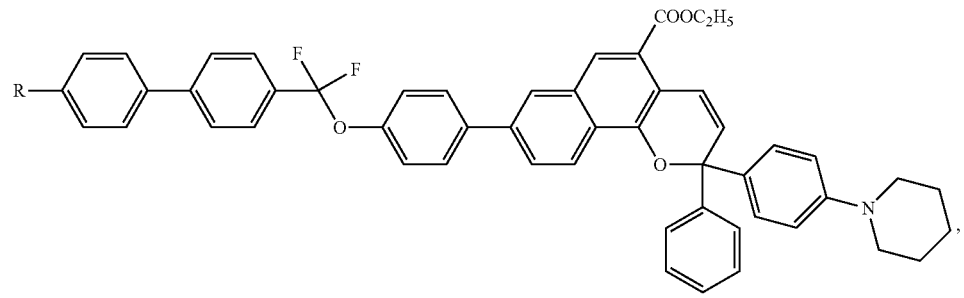

wherein R is $C_{1-12}$ alkyl group.

6. The optical device as claimed in claim 4, wherein the photo responsive material has a chemical structure of:

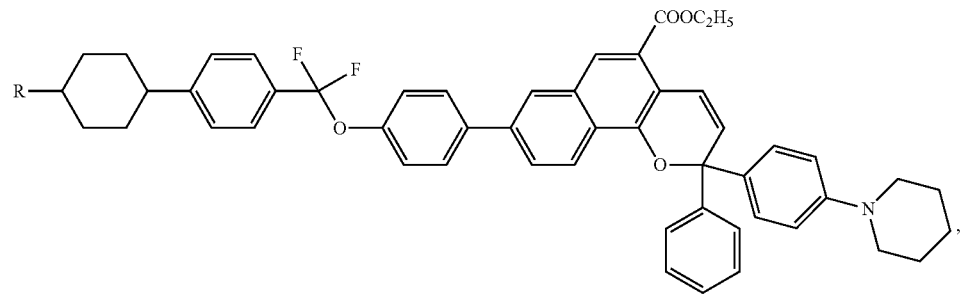

wherein R is $C_{1-12}$ alkyl group.

* * * * *